Figure 1:
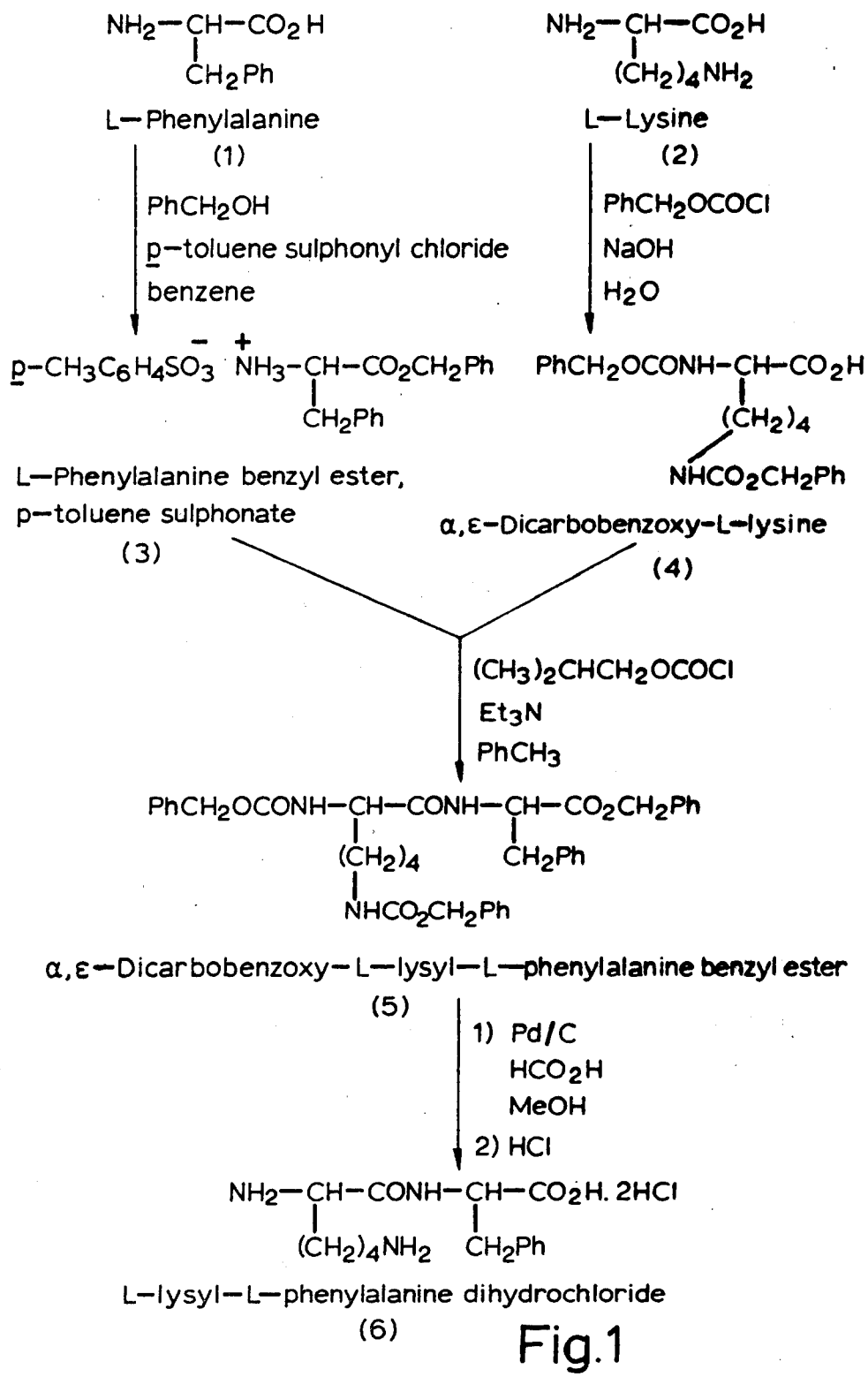

United States Patent [19]

Collinson-Jones et al.

[11] 4,376,766

[45] Mar. 15, 1983

[54] ANTI-SICKLING AGENTS

[75] Inventors: Rosalind I. Collinson-Jones, Jordans; John F. Pardon, High Wycombe, both of England

[73] Assignee: G.D. Searle & Co., Skokie, Ill.

[21] Appl. No.: 286,416

[22] Filed: Jul. 24, 1981

[30] Foreign Application Priority Data

Aug. 1, 1980 [GB] United Kingdom ................. 8025178

[51] Int. Cl.³ ...................... A61K 37/02; C07C 103/52
[52] U.S. Cl. .............................. 424/177; 260/112.5 R
[58] Field of Search .................. 424/177; 260/112.5 R

[56] References Cited

U.S. PATENT DOCUMENTS 4,261,980  4/1981  Cort .................................... 424/177

OTHER PUBLICATIONS

George R. Pettit, *Synthetic Peptides*, Elsevier Scientific Publishing Company, NY., 1980, V, p. 157.

*Primary Examiner*—Delbert R. Phillips
*Assistant Examiner*—F. T. Moezie
*Attorney, Agent, or Firm*—Albert Tockman; Robert H. Benson

[57] ABSTRACT

The use of an anti-sickling agent of one or more of L-lysine-L-phenylalanine, L-lysine-L-tyrosine, L-histidine-L-lysine-L-tyrosine-L-histidine, in particular L-lysine-L-phenylalanine, and salts thereof is disclosed.

An anti-sickling composition which comprises one or more of L-lysine-L-phenylalanine, L-lysine-L-tyrosine, L-histidine-L-lysine-L-tyrosine-L-histidine and salts thereof in association with one or more sterile, pharmaceutically-acceptable carriers, diluents and adjuvants is also disclosed.

11 Claims, 9 Drawing Figures

ANTI-SICKLING AGENTS

This invention relates to anti-sickling agents; more particularly, it relates to the use of certain small peptides, in particular the dipeptide L-lysine-L-phenylalanine, as anti-sickling agents.

Persons having homozygous sickle cell disease have an inherited abnormality of the haemoglobin brought about by a single mutation in the gene coding for the haemoglobin β-chain in that the single amino acid glutamic acid at position six in normal haemoglobin is replaced by the amino acid valine. "Sickle cell anaemia" is the name given to the resultant condition for persons having two genes for the abnormal haemoglobin. The condition is characterised by abnormally shaped red blood cells. In oxygenated blood, the cells appear normal having a discoidal shape, but when deoxygenated, the red cells become sickle-shaped and are less able to pass through small blood vessels due to the more rigid nature thereof.

The consequences of the defect are haemolytic anaemia and tissue damage brought about by the blockage of blood vessels by the sickled cells. Complications may be severe and include retarded growth, periodic attacks of pain and progressive organ dysfunction leading in most instances to a much reduced life expectancy. In persons having one gene for sickle haemoglobin and one for normal haemoglobin ("sickle cell trait") the proportion of normal red blood cells is sufficiently high to eliminate most of the problems encountered by persons having both genes mutated ("sickle cell disease").

The changes in the red cell during sickle cell crises may be explained by specific interactions that occur between haemoglobin molecules. Under normal physiological conditions haemoglobin (HbA) molecules do not form specific aggregates. However, deoxygenated sickle cell haemoglobin (HbS) molecules tend to form fibrils which associate to produce bundles. The parallel association of fibrils into stiff bundles induces characteristic deformation and rigidity in the red blood cells. X-ray crystallographic studies of deoxygenated sickle cell haemoglobin (see, for example, Wishner, B. C., et al, (1975), J. Mol. Biol., 98, 179–194) and confirmatory X-ray fibre diffraction (see, for example, Magdoff-Fairchild, B., and Chiu, C., Proc. Natl. Acad. Sci. U.S.A., 76, 1, 223–226) demonstrate the tendency for fibril formation and reveal the sites on the HbS molecule where interactions occur. One of the sites for interaction between fibrils is the modified region of the β-chain containing valine 6. This region in a β-chain in one sub-unit interacts with the region β Phe (85)-β Leu (88) in a neighbouring sub-unit. Apparently, this increased interaction between Hb molecules is a cause of the formation of Hb bundles and aggregates. Thus, an agent which binds to one or both of these sites of interaction, to block interactions, is to be expected to reduce the formation of bundles or aggregates and subsequently to reduce the sickling tendency.

Another approach to the prevention of sickling is to increase the oxygen affinity of haemoglobin since the fibril and bundle formation only occurs in deoxygenated haemoglobin. Currently, the clinical treatment for sickle cell disease is to reduce the symptoms by eliminating as many causative factors, e.g. exposure to cold, reduced air pressure and infections, as possible. Regular prophylactic treatment with antibiotics and vitamins in sometimes adopted. A number of compounds acting both covalently and non-covalently have been investigated to modify either HbS or the red cell in an effort to prevent aggregation of HbS and sickling. These include:

(a) Nitrogen mustard: Roth, E. F., et al, (1972), Biochem. Biophys. Res. Comm., 48, 612–618.

(b) Aspirin derivatives: Walder, J. A., et al, (1977), Proc. Natl. Acad. Sci. U.S.A., 74, 5499–5503.

(c) Cyanate: Cerami, A., (1972), N. Engl. J. Med., 287 807–812.

(d) Anionic pyridoxal derivative: Benesch, R., et al (1977), Proc. Natl. Acad. Sci. U.S.A., 74, 1721–1723.

(e) Aldehydes: Zaugg, R. H., et al, (1977), J. Biol. Chem., 252, 8542

(f) Bifunctional cross-linking agents: Lubin, B. H. et al, (1975), Proc. Natl. Acad. Sci. U.S.A., 72, 43–46.

(g) Alkyl ureas: Elbaum, D., et al, (1974), Proc. Natl. Acad. Sci. U.S.A., 71, 4718–4722.

(h) Urea: Cerami, A., and Manning, J. M., (1971), Proc. Natl. Acad. Sci. U.S.A., 68, 1180–1183.

(i) Amino acids: Noguchi, C. T., and Schechter, A. N., (1978), Biochemistry, 17, 5455–5459. Gorecki, M., et al, (1980), Proc. Natl. Acad. Sci. U.S.A., 77, 181–185.

(j) Small peptides: Votano, J. R., et al, (1977), Science, 196, 1216–1219. Kobata, S., and Yang, J. T., (1977), Proc. Natl. Acad. Sci. U.S.A., 74, 5431–5434.

The use of tri- and tetra-peptides as inhibitors of HbS aggregation has been suggested by Votano, J. R., (loc cit), but most dipeptides were discounted as inactive. Oligopeptides reproducing the sequence in the binding regions in the HbS polymers have been found to be unsuccessful competitors for sites (see Kobata, S., and Yang, J. T., (loc cit)). Gorecki et al (loc cit) have suggested benzylated-phenylalanine and derivatives thereof as inhibitors of whole cell sickling with low activity against HbS polymerisation (gelation). Comparison of the behaviour of phenylalanine compounds or analogues thereof as HbS gelation inhibitors (see, for example, Behe, M. J., and Englander, S. W., (1979) Biochemistry, 18, 4196–4201; Gorecki, M., et al, (1980), Biochem 19, 1564–1568; and Noguchi, C. T., et al (loc cit)) show that the solubility of HbS is not significantly improved over that due to L-phenylalanine.

It has now surprisingly been found that the dipeptide L-lysine-L-phenylalanine increases HbS solubility by four-fold over L-phenylalanine and, moreover, inhibits whole cell sickling. The dipeptide L-lysine-L-phenylalanine, the related dipeptide L-lysine-L-tyrosine and the tetrapeptide L-histidine-L-lysine-L-tyrosine-L-histidine have now been found to inhibit the gelation of deoxygenated HbS solutions in vitro. The solubility of HbS in the presence of the anti-sickling agent is increased to a level comparable to that of HbAS (haemoglobin from heterologous "trait" blood). Moreover, the onset of gelation of deoxygenated HbS solutions in the presence of the anti-sickling agent is delayed. Furthermore, it has also surprisingly been found that the number of cells sickling at low oxygen pressures, as observed using a light microscope, is substantially reduced by incubation with L-lysine-L-phenylalanine and that the cells show a concomitant increase in oxygen affinity.

Accordingly, the present invention relates to the use as an anti-sickling agent of one or more of L-lysine-L-phenylalanine, L-lysine-L-tyrosine, L-histidine-L-lysine-L-tyrosine-L-histidine and salts thereof.

The peptides may be produced in known manner. The tetrapeptide, for example, may be synthesised using methods described by Merrifield, R. B., (1963), JACS, 85, 2149–2154, and the dipeptide L-lysine-L-phenylalanine, for example, may be produced using methods described by El Amin, B., et al, (1979), JOC, 44, (19), 3442. The purity of the product may be assessed by NMR, TLC and MS.

For purposes of exemplification, L-lysyl-L-phenylalanine dihydrochloride may be produced by the reaction scheme illustrated in FIG. 1 of the accompanying drawings. This procedure may be regarded as a modification of a number of known methods (see, for example, Izumiya, N., and Makisumi, S., (1957), J. Chem. Soc. Japan, 78, 662; Bergmann, M., et al, (1935), J. Biol. Chem., 111. 245; Schwarz, H., and Arakawa, K., (1959), JACS, 81, 5694; Inzumiya, N., et al, (1964), Bull. Soc. Chim. Japan, 37, (12), 1809; and El Amin, B., et al, loc cit).

It was found that the conditions described by Izumiya and Makisumi to protect L-phenylalanine (1) as the benzyl ester, p toluene sulphonate salt (3) resulted in total racemisation of the product. Further investigation showed that the milder Schwarz-Arakawa procedure gave optically pure (3). L-lysine was protected as the dicarbobenzoxy derivative (4) according to Bergmann et al. (4) was then coupled with (3) via a mixed anhydride reaction (Izumiya et al) using iso-butyl chloroformate in toluene with triethylamine as base to give the protected dipeptide (5). The deprotection of (5) was effected via catalytic transfer hydrogenation in methanol using 10 wt % palladium on charcoal as catalyst and formic acid as hydrogen donor (El Amin). This procedure is rapid and efficient compared to conventional catalytic hydrogenation. The product, in the form of the formate of the dipeptide, was converted to the dihydrochloride by addition of 2 mol equivalents of HCl.

The experimental details of such a production are given below.

The present invention also relates to an anti-sickling composition which comprises one or more of L-lysine-L-phenylalanine, L-lysine-L-tyrosine, L-histidine-L-lysine-L-tyrosine-L-histidine and salts thereof in association with one or more sterile, pharmaceutically-acceptable carriers, diluents or adjuvants.

According to the present invention, the preferred anti-sickling agent is L-lysine-L-phenylalanine, which is readily soluble in physiological buffers.

A number of in vitro methods have been developed for testing the effects of compounds of the functioning of HbS molecules. One such method determines the ability of a compound to inhibit gel formation in HbS solutions. In this gelation assay, Hb solution in phosphate buffer, pH 7.0, at physiological concentrations are mixed at 0° C. with the test compound and deoxygenated by evacuation. Polymerisation does not occur at this low temperature. The solutions are then transferred to centrifuge tubes and equilibrated at 37° C. for 30 minutes before centrifugation at 150,000 g for 1 hour. The supernatant is decanted from the gel and the Hb concentration (Csol) thereof determined spectrophotometrically. For sickle cell haemoglobin without addition of anti-sickling agent, the Csol is typically 17 gm/dl. This compares with a Csol of 23 gm/dl for haemoglobin extracted from individuals having sickle cell trait. Such individuals do not suffer the crises or the symptoms experienced by individuals having sickle cell disease.) Thus, an agent which has the ability to increase Csol from 17 gm/dl to 23 gm/dl at low molar concentrations has the potential to prevent sickling.

The rate of polymerisation of HbS molecules may be followed by spectrophotometrically monitoring the onset of gelation, after a temperature jump from 0° C. to 37° C., in a concentrated HbS solution. An effective anti-sickling agent should reduce the rate of polymerisation by at least ten-fold.

The uptake of oxygen by haemoglobin as a function of oxygen pressure gives a measure of the oxygen affinity of the haemoglobin and is often described by the value of $P_{50}$, i.e. the pressure of oxygen at which haemoglobin is 50% saturated with $O_2$. The $P_{50}$ for HbS is typically higher than that for HbA, the decreased affinity for $O_2$ compensating for the anaemia associated with the disease by facilitating release of $O_2$ to the tissues. An agent which would decrease the $P_{50}$ of HbS would cause the deoxy-form of the molecule to be less favoured and would thus inhibit polymerisation. It is possible to correlate the degree of oxygenation of sickle erythrocytes with the ability thereof to assume sickled morphology by counting deoxygenated cells using a light microscope. An anti-sickling agent which reduces the number of sickled cells produced at low oxygen concentrations would be effective in preventing or diminishing a crisis.

Figure 2:
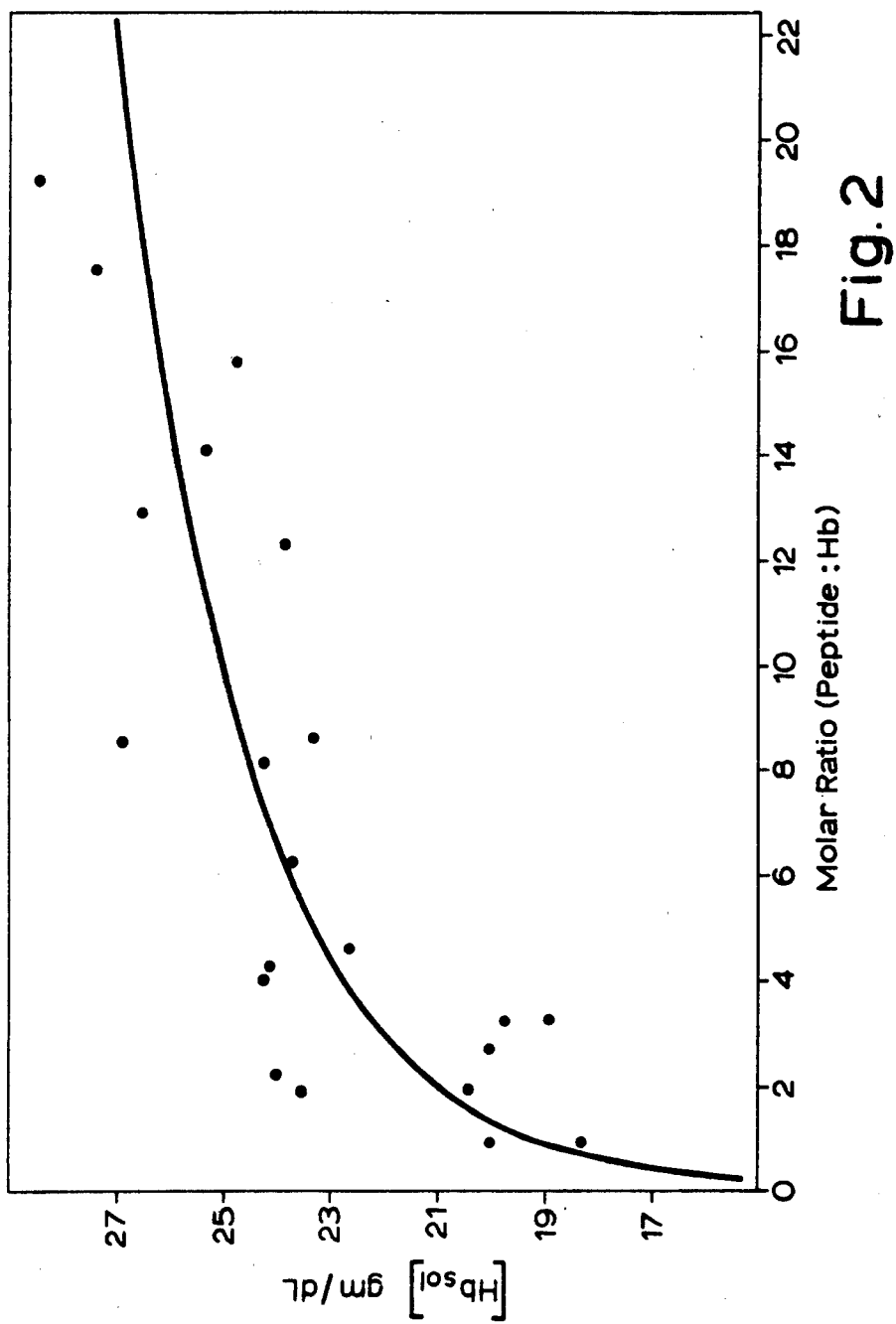

FIG. 2 of the accompanying drawings presents HbS gelation assay results which illustrate the effect of L-lysine-L-phenylalanine on the solubility (Csol) of homozygous sickle cell haemoglobin. The increase in Csol demonstrates the ability of this compound to restrict the formation of high molecular weight association of haemoglobin molecules. A plot of Csol versus log (peptide:Hb) is linear and has a Csol of 23 for the peptide:Hb tetramer ratio of 4.7:1. Thus, if a compound: Hb tetramer ratio of 5:1 may be accomplished in the red cell, the symptoms of sickle cell disease should be alleviated. Significant reductions in the severity of the disease may be expected for lower levels of anti-sickling agent. For comparison purposes, corresponding data for the dipeptides L-lysine-L-serine and L-aspartic acid-L-phenylalanine show no significant rise in Csol. This may be taken to demonstrate the requirement for aromatic and positively-charged moieties respectively in the compound.

Figure 3:
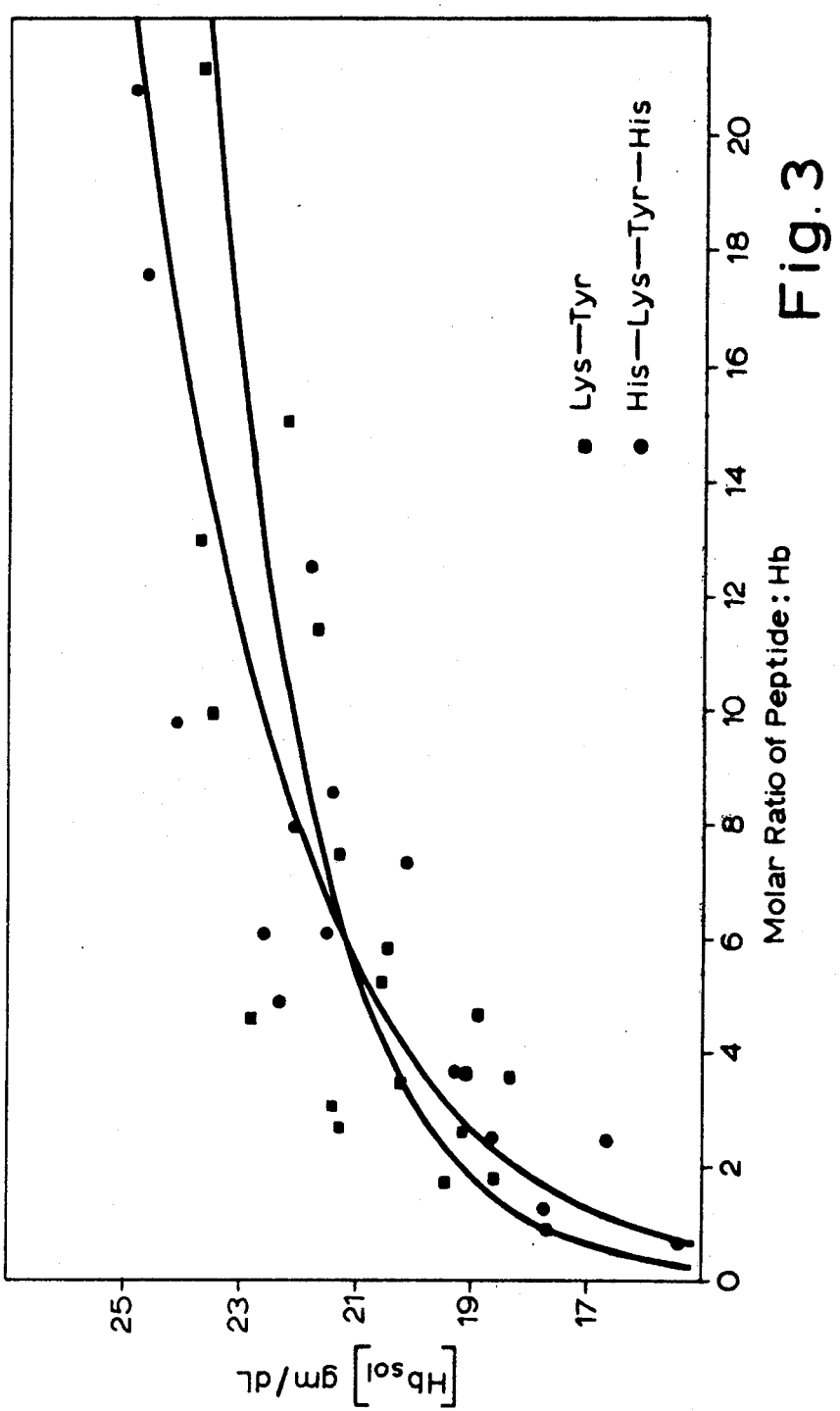

The data presented in FIG. 3 of the accompanying drawings from other HbS gelation assays illustrate the anti-polymerisation effects of L-lysine-L-tyrosine (Lys-Tyr) and L-histidine-L-lysine-L-tyrosine-L-histidine (His-Lys-Try-His) by showing the effect thereof on solubility of HbS.

Figure 4:
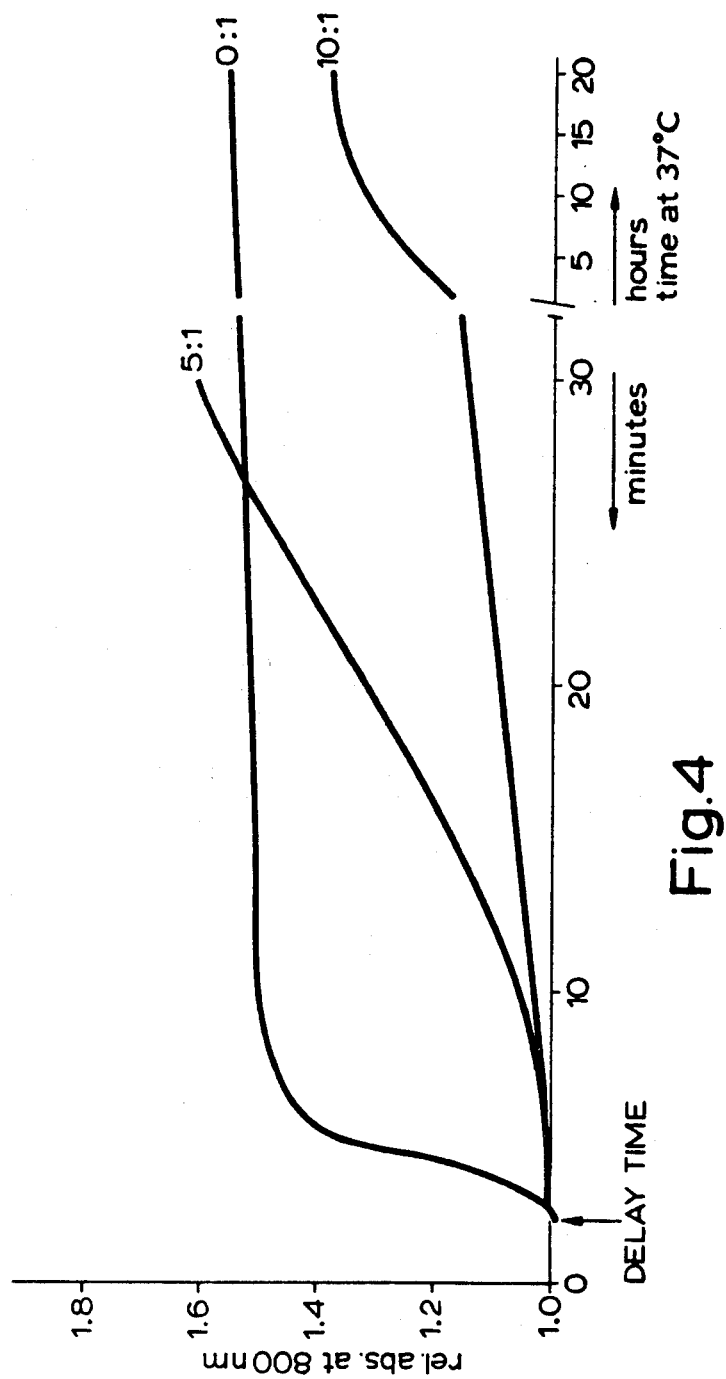

FIG. 4 of the accompanying drawings illustrates the effect of different ratios of L-lysine-L-phenylalanine: HbS on lag time before gelation (i.e. on rate of polymerisation) and shows the increase in the delay before gelation of HbS induced by the anti-sickling agent at different molar ratios of dipeptide:HbS.

Figure 5:
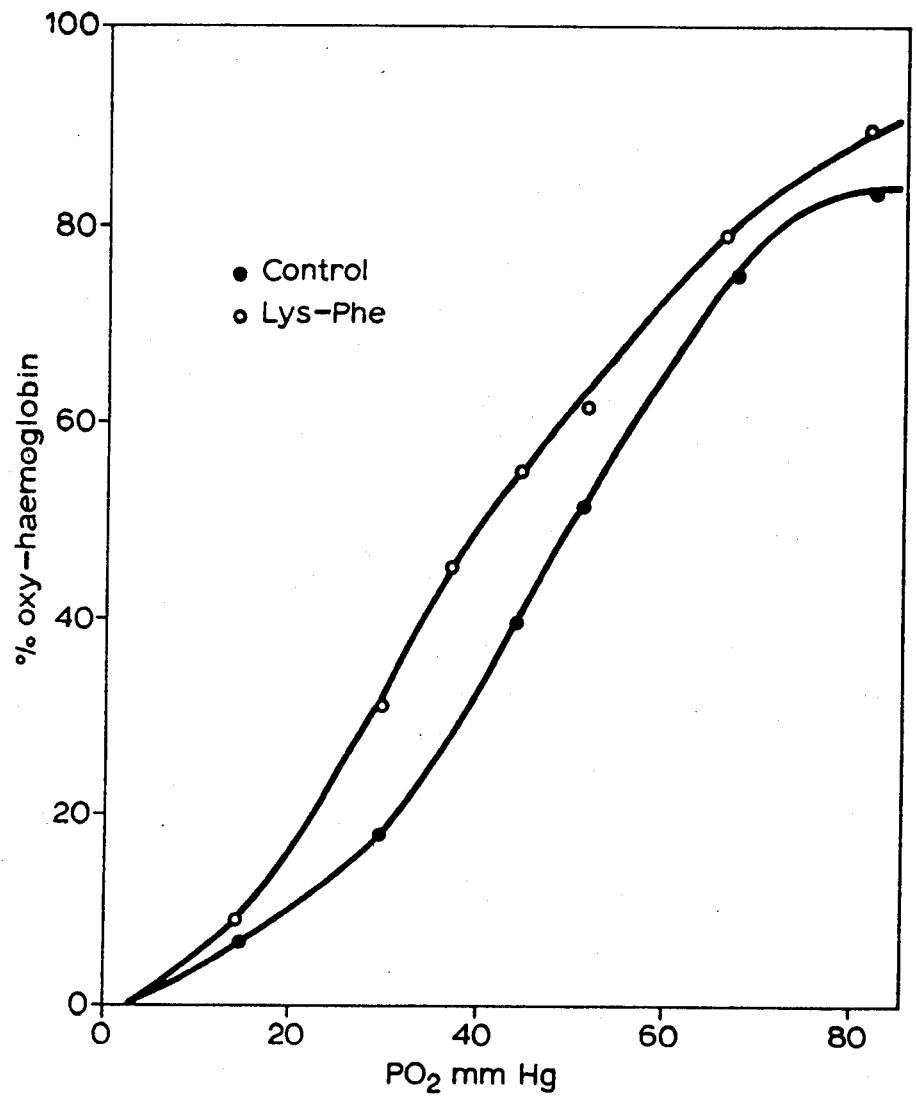

FIG. 5 of the accompanying drawings illustrates an oxygen dissociation curve for HbS in the absence and presence of L-lysine-L-phenylalanine (Lys-Phe), (SS cells+25 mM L-lysine-L-phenylalanine, 3 hours incubation at 37° C.) and shows the effect of the anti-sickling agent on the oxygen affinity of sickle cells. The $P_{50}$ value was found to reduce from 51 mm to 41 mm of mercury by a 5:1 molar ratio of extra-cellular dipeptide:intra-cellular HbS.

Figure 6:
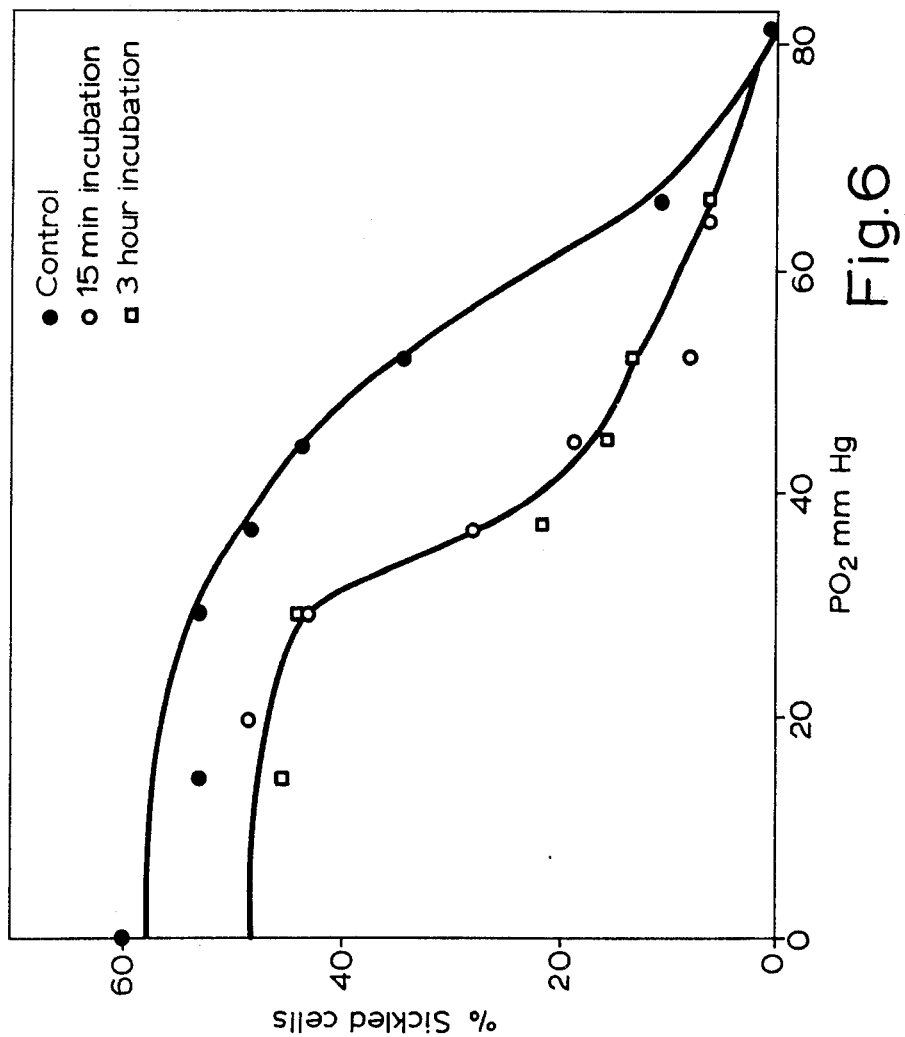

FIG. 6 of the accompanying drawings illustrates a microscopic assay of whole sickle cells with and without Lys-Phe at different partial pressures of oxygen and having different preincubation times and shows that the percentage of sickled cells is reduced when the blood is pre-incubated with L-lysine-L-phenylalanine. There are fewer sickle cells in the presence of the dipeptide over the entire range of oxygen concentration. Moreover, as oxygen is made available to the sickled cells, a greater proportion becomes unsickled in the presence of L-lysine-L-phenylalanine than in the control. In vivo, this increased reversibility would reduce the number of circulating irreversibly sickled cells (ISC).

Figure 7:
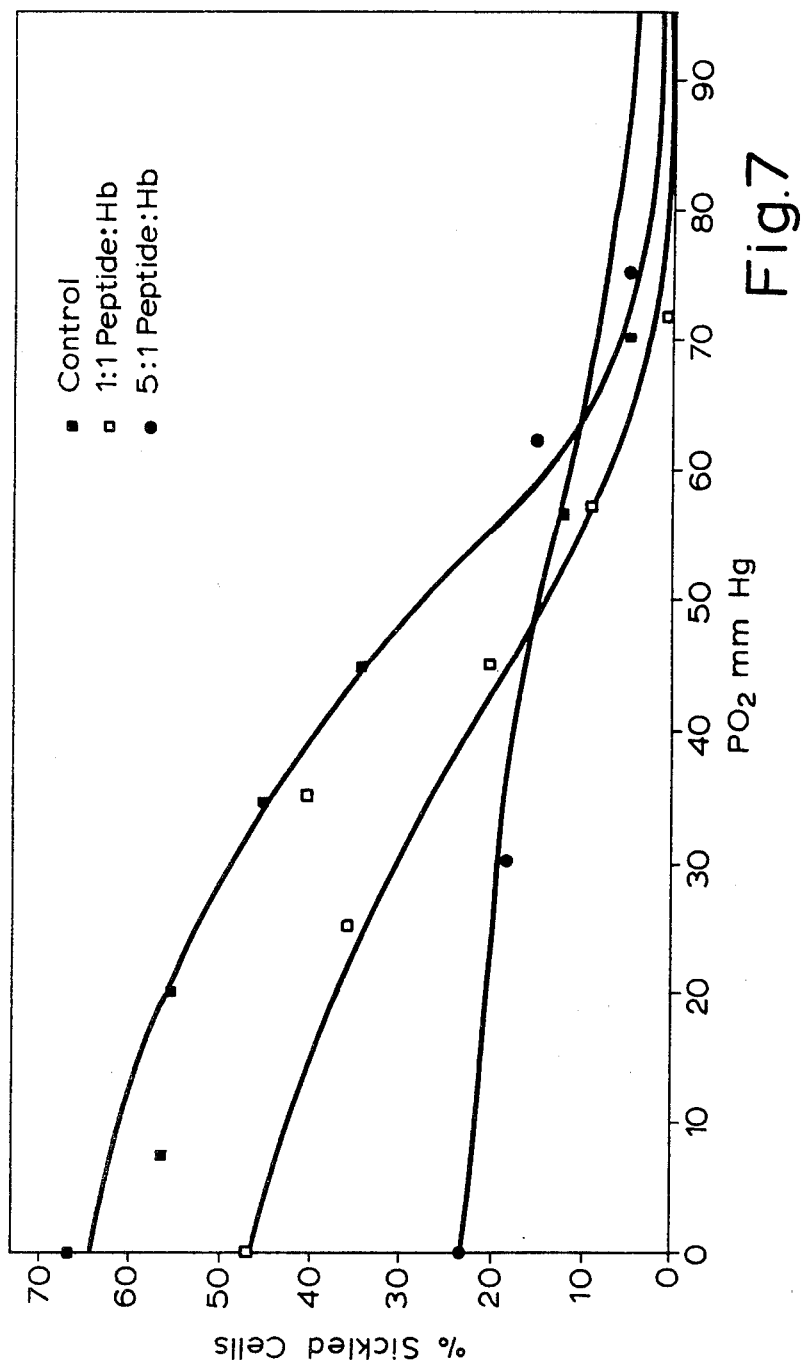

FIG. 7 of the accompanying drawings illustrates a similar whole cell assay for the dipeptide L-lysine-L-tyrosine at different partial pressures of oxygen and at two molar ratios of dipeptide:haemoglobin and shows a reduction in the percentage of sickled cells by pre-incubation with the dipeptide.

Figure 8:
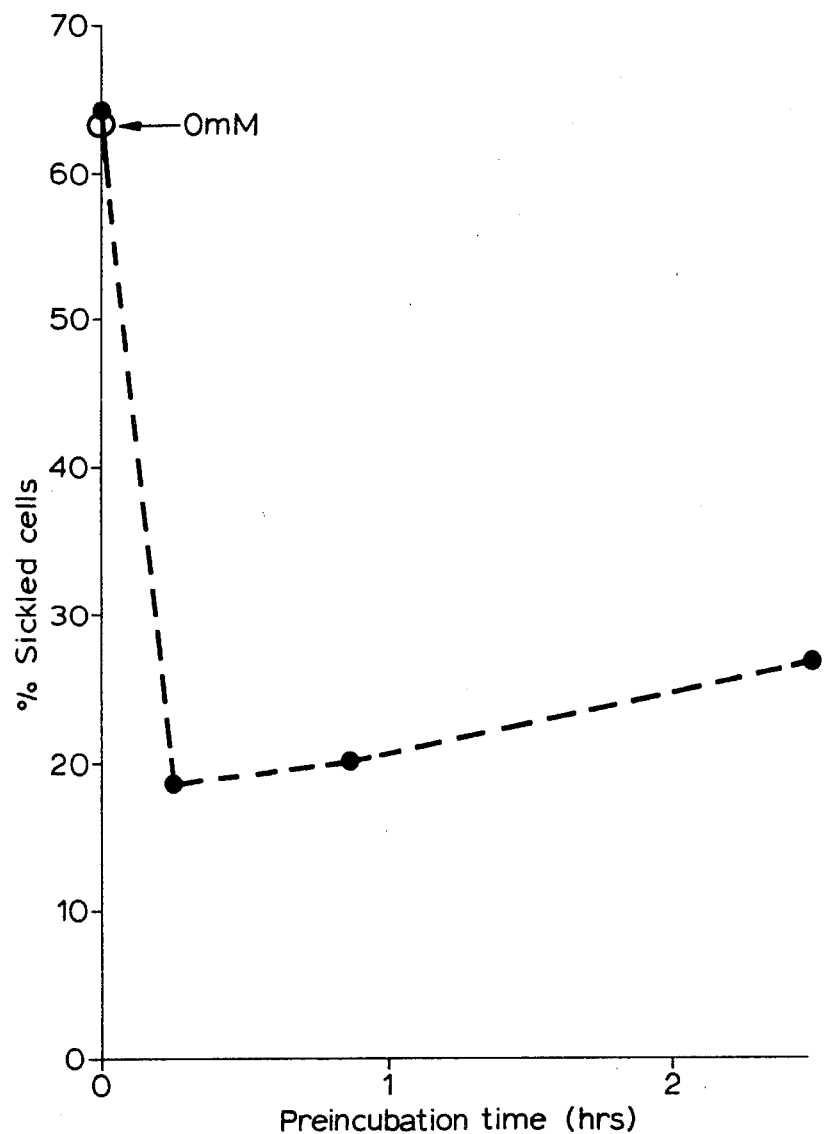

FIG. 8 of the accompanying drawings illustrates the effect of pre-incubation with L-lysine-L-phenylalanine on sickling in a whole cell sickling assay at zero oxygen tension and further shows that pre-incubation for 15 minutes is sufficient to protect against sickling. (The zero time points correspond to the results obtained with the control sickle blood and with sickle blood with Lys-Phe.

Figure 9:
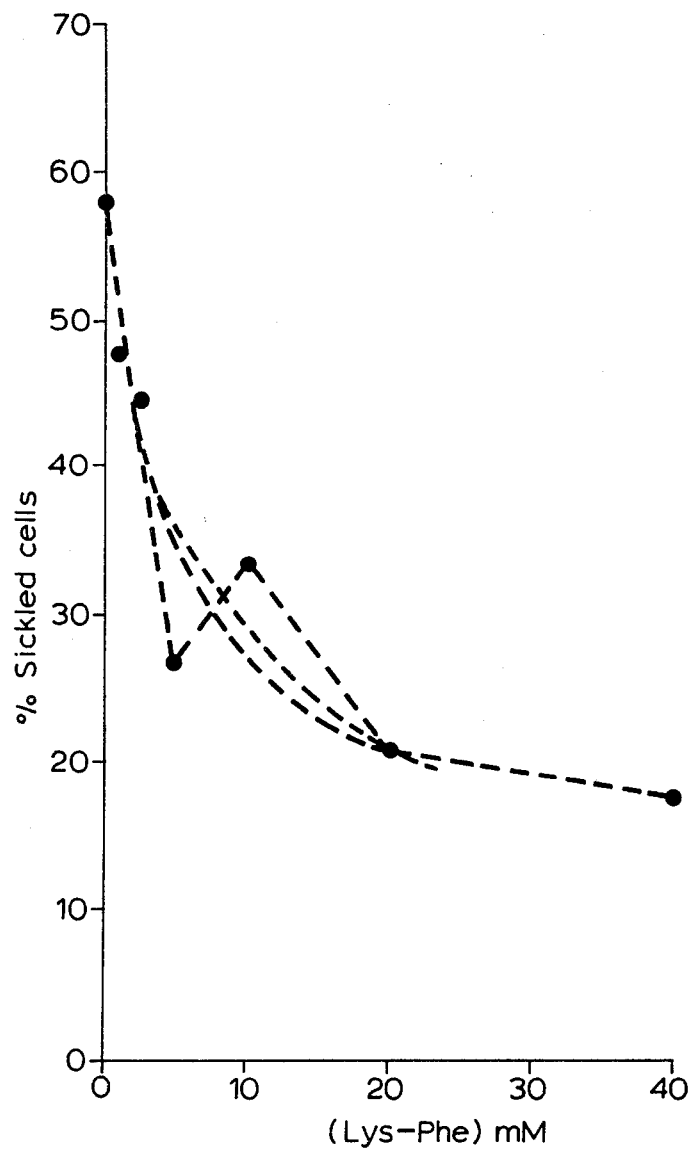

FIG. 9 of the accompanying drawings illustrates a dose response curve in vitro showing the effect of different concentrations of L-lysine-L-phenylalanine on sickling in a microscope assay under conditions of complete deoxygenation. An extra-cellular concentration of dipeptide of about 5 millimolar was found to be sufficient to reduce the number of sickled cells by 50%.

Patients having sickle cell disease may be treated extra-corporeally or, preferably intravenously in accordance with the present invention. Extra-corporeal treatment may be accomplished by treating the blood, after removal from the patient, with a solution containing the anti-sickling agent in association with one or more pharmaceutically-acceptable carriers or diluents and then returning the blood to the patient.

Preferably, treatment may be effected by injecting directly into the blood-stream of the patient a pharmaceutical composition comprising a non-toxic, anti-sickling effective amount of the active ingredient, preferably L-lysine-L-phenylalanine, or mono- or di-salts thereof and one or more suitable carriers or diluents, such as sterile buffer to maintain a pH of 7.4, the level of human blood.

Alternatively, treatment may be effected by the oral administration of the anti-sickling agent, preferably L-lysine-L-phenylalanine or salts thereof, in association with a pharmaceutically-acceptable carrier or diluent.

An anti-sickling effective dose of the active ingredient in accordance with the present invention will vary from patient to patient and will depend, inter alia, upon the severity of the condition. In general however, a per diem dose within the range of from 10 to 150 mg/kg, preferably from 20 to 80 mg/kg, is suitable. This may be administered as a single dose or as a number of doses.

In the case of oral or sub-lingual administration, the active ingredient may be formulated in dosage unit form as a tablet or capsule, for example. Such dosage unit may conveniently contain from 5 to 200 mg, preferably from 20 to 100 mg, of active ingredient.

Conventional slow-release formulations may also be used.

In the case of administration by injection, the dose regimen will be such as to correspond to the dosage outlined above.

The agent may also be administered by subcutaneous implantation.

As indicated above, the active ingredients may be in the form of the corresponding bases or salts, in particular acid addition salts, such as hydrochlorides. Mono- or di-salts may be used. When the compounds are administered as salts, in particular di-salts, the material should be buffered to a physiological pH.

More particularly, the anti-sickling peptides are commonly available as the mono-hydrochlorides.

The preferred agent, L-lysine-L-phenylalanine, is also used in the form of the di-hydrochloride and the mono-hydrobromide for example.

The pharmaceutical compositions may be produced by conventional techniques which are described, inter alia, in Remington's Pharmaceutical Science, Mach Publishing Co. Easton, Penn. U.S.A., 1965.

For example tablets may be produced by grinding the active ingredients to a fine powder, blending with starch and lactose and moistening with water, prior to granulation. The granule mass is then milled, blended with magnesium stearate and compressed into tablets.

It may be desirable to coat tablets in order to protect the active ingredient from degradation during passage through the stomach (enteric coating).

As indicated above, the preferred formulation is as a buffered solution, in particular for administration by injection.

An injectable formulation for slow intravenous infusion would typically comprise a sterile aqueous solution adjusted to the desired pH with sodium hydroxide or weak buffer, such as a sodium salt of phosphoric acid, and rendered isotonic using for example, sodium chloride or dextrose.

Production of L-lysyl-L-phenylalanine dihydrochloride:

(Reference numerals refer to the reaction scheme illustrated in FIG. 1 of the accompanying drawings.)

L-phenylalanine benzyl ester, p-toluene sulphonate (3):

A mixture of L-phenylalanine (420 mmol, 69.38 g) p-toluene sulphonic acid (511 mmol, 97.01 g), benzyl alcohol (4.06 mol, 438.91 g) and benzene (1.5 l) was heated under reflux, with stirring, for 5 hours with azeotropic removal of water using a Dean & Stark apparatus. All solid was in solution after ca. 20 min.

Removal of benzene using a rotary evaporator at 45° C., followed by trituration of the resulting oil with ether (1.5 l), gave a white crystalline solid which was filtered, washed with ether (800 ml) and dried in air. The crude product was recrystallised from ethanol (400 ml)/ether (400 ml), washed by heating under reflux for 15 minutes with ether (1.5 l) and dried overnight at room temperature/0.1 torr giving a white solid. Yield 149.73 g (83.4%); TLC (cellulose plate; n-BuOH:HoAc:-Pyridine:H$_2$O; (vol) 60:12:40:48; ninhydrin); single spot; mp 170°–171° (lit 164°–165.5°); $[\alpha]_D^{20}$+7.33° (C=2, DMF), (lit+7.8°).

α,ε-dicarbobenzoxy-L-lysine (4):

To a stirred solution of L-lysine monohydrochloride 300 mmol, 54.80 g) in 2 N sodium hydroxide solution (600 mmol, 300 ml) cooled to 5° C., was added simultaneously from two separate dropping funnels, benzyl chloroformate (600 mmol, 102.36 g) and 4 N sodium hydroxide solution (600 mmol, 150 ml), at such a rate that the addition lasted 50 minutes, the temperature of the reaction mixture did not rise above 5° C. and the pH did not fall below 11.5. A white emulsion formed which was stirred at ambient temperature overnight.

The reaction mixture was washed with ether (1.2 l) cooled to 10° C. and acidified to congo red indicator by slow addition of concentrated hydrochloric acid (43 ml). Extraction with chloroform (3×600 ml), followed by drying over sodium sulphate and removal of solvent using a rotary evaporator gave a colourless oil which was allowed to stand overnight at ambient temperature/0.1 torr giving 109.32 g (88%) of (4); $[\alpha]_D^{20} - 3.68°$ (C=2 ethanol), TLC (silica, n-BuOAc) single spot under short wavelength UV (254 nm).

α,ε-dicarbobenzoxy-L-lysyl-L-phenylalanine benzyl ester (5)

To a stirred solution of α,ε-dicarbobenzoxy-L-lysine (4) (96 mmol, 39.69 g), toluene (310 ml) and triethylamine (96 mmol, 9.70 g) at 0° C., was added, over a period of 15 minutes, iso-butyl chloroformate (109 mmol, 14.88 g), maintaining the temperature between −5° and 0° C. The resulting jelly-like reaction mixture was stirred for 30 minutes at 0° C. and then a slurry of L-phenylalanine benzyl ester, p-toluene sulphonate (1) (96 mmol, 40.99 g) in chloroform (470 ml) and triethylamine (96 mmol, 9.70 g) was added quickly in one portion and the clear solution was allowed to stir at ambient temperature overnight.

The reaction mixture was washed with 4% (w/v) sodium bicarbonate solution (2×900 ml), 2% (w/v) hydrochloric acid (2×900 ml) and water (2×320 ml). Drying over sodium sulphate, followed by removal of solvent using a rotary evaporator gave a white solid which was recrystallised from a mixture of hexane (350 ml) and benzene (700 ml). The white crystalline solid was washed with hexane (200 ml) and dried at ambient temperature/0.1 torr, giving 41.96 g (67%) of (5), mp 139°-142°, TLC (silica, n-BuOAc) single spot under short wavelength UV (254 nm), $[\alpha]_D^{20} - 4.45$ (C=2, chloroform).

L-lysyl-L-phenylalanine dihydrochloride (6):

10 wt % palladium on charcoal catalyst (25 g, Engelhard Code No. 99816) was placed in a 5 liter flask and purged with nitrogen. Formic acid (4.4% (w/v) in methanol, 1.5 l) was added, followed by a slurry of the protected dipeptide (5) (38.40 mmol, 25.00 g) in methanol (1 l). After stirring at room temperature for 45 minutes, the reaction mixture was filtered through "hyflo" and evaporated to dryness using a rotary evaporator giving a clear oil, the crude formate salt.

The oil was dissolved in water (200 ml) and 1 N hydrochloric acid (76.8 ml, 76.8 mmol) was added. Evaporation to dryness at 40° C. using a rotary evaporator gave a very pale yellow oil which was dissolved in water (300 ml) and freeze dried to give (6) as an amorphous powder in 80% yield (11.27 g). TLC (1) Polygram Cel 300 DEAE/HR-2/15 plate n-BuOH:HOAc:Pyridine:H$_2$O; (vol) 60:12:40:48, ninhydrin spray; and (ii) silica 60F$_{254}$, Propan-2-ol:8:80 ammonia; (vol) 70:30, ninhydrin spray, both show a purity of >98% by dilution analysis, $[\alpha]_D^{20} + 23.2°$ (C=1.015, ethanol), MS m/e 367 (M+1)+.

What is claimed is:

1. A pharmaceutical composition of use in the treatment of sickle cell disease comprising, as active ingredient, an anti-sickling amount of a compound selected from the group consisting of L-lysine-L-phenylalanine, L-lysine-L-tyrosine and pharmaceutically-acceptable salts thereof in association with a pharmaceutically-acceptable carrier or diluent.

2. The composition according to claim 1 adapted for injection.

3. The composition according to claim 1 adapted for oral or sub-lingual administration.

4. The composition according to claim 3 in dosage unit form, each dosage unit containing from 5 to 200 mg of active ingredient.

5. The composition according to claim 4 wherein each dosage unit contains from 20 to 100 mg of active ingredient.

6. A method for the alleviation of sickle cell disease in a patient suffering therefrom comprising administering to said patient an anti-sickling effective amount of a compound selected from the group consisting of L-lysine-L-phenylalanine, L-lysine-L-tyrosine and pharmaceutically-acceptable salts thereof.

7. The method according to claim 6 wherein the anti-sickling effective amount is within the range of from 10 to 150 mg/kg.

8. The method according to claim 7 wherein the anti-sickling effective amount is within the range of from 20 to 80 mg/kg.

9. The method according to claim 6 wherein said administration is effected by injection.

10. The method according to claim 6 wherein said administration is effected extra-corporeally.

11. The method according to claim 6 wherein said administration is effected orally or sub-lingually.

* * * * *